(12) United States Patent
Pollock

(10) Patent No.: US 10,918,556 B2
(45) Date of Patent: Feb. 16, 2021

(54) THERAPEUTIC SUPPORT FOR BEING WORN BY A SUBJECT

(75) Inventor: Cheryl Leonie Pollock, Hornsby (AU)

(73) Assignee: CHEZLEON PTY LIMITED, Waratah (AU)

( * ) Notice: Subject to any disclaimer, the term of this patent is extended or adjusted under 35 U.S.C. 154(b) by 0 days.

(21) Appl. No.: 14/412,860

(22) PCT Filed: Aug. 3, 2012

(86) PCT No.: PCT/AU2012/000931
§ 371 (c)(1),
(2), (4) Date: Jan. 16, 2015

(87) PCT Pub. No.: WO2014/005170
PCT Pub. Date: Jan. 9, 2014

(65) Prior Publication Data
US 2015/0133836 A1   May 14, 2015

(30) Foreign Application Priority Data
Jul. 6, 2012   (AU) ................................ 2012902897

(51) Int. Cl.
*A61H 1/00*   (2006.01)
*A61F 5/30*   (2006.01)
(Continued)

(52) U.S. Cl.
CPC ............... *A61H 1/008* (2013.01); *A61F 5/30* (2013.01); *A61F 13/085* (2013.01); *A61F 13/145* (2013.01)

(58) Field of Classification Search
CPC ...... A61H 1/006–008; A61H 11/00–02; A61H 2201/0103; A61H 2209/00;
(Continued)

(56) References Cited

U.S. PATENT DOCUMENTS 4,370,754 A * 2/1983 Donzis ............... A41D 13/0153
                                                    2/16
5,403,265 A   4/1995 Berguer et al.
(Continued)

FOREIGN PATENT DOCUMENTS

WO   2005097020   10/2005

OTHER PUBLICATIONS

International Search Report dated Nov. 6, 2012 in International Application No. PCT/AU2012/000931. (3 pages).

*Primary Examiner* — Rachel T Sippel
(74) *Attorney, Agent, or Firm* — Shutts & Bowen LLP

(57) ABSTRACT

A flexible therapeutic support (32, 35, 40, 48, 54) for the prophylaxis or treatment of the accumulation of a fluid in the body of a subject. The therapeutic support has a plurality of protruberances (14) for respectively applying localised pressure to an area of the subject's body with, or subject to, accumulation of the fluid, the support being configured to be worn by the subject over the area and press the protruberances (14) against the body of the subject, and the protruberances being spaced apart from one another about the face (12) of the support. There are also provided methods for the prophylaxis or treatment of the accumulation of a fluid in the subject's body. The accumulated fluid can, for instance, be lymphoedema or other form of oedema.

18 Claims, 7 Drawing Sheets

(51) Int. Cl.
*A61F 13/14* (2006.01)
*A61F 13/08* (2006.01)

(58) Field of Classification Search
CPC .......... A61F 5/30–34; A61F 13/08–085; A61F 13/143–146; A61F 2013/0028
See application file for complete search history.

(56) References Cited

U.S. PATENT DOCUMENTS

| | | |
|---|---|---|
| RE35,113 E * | 12/1995 | Grim ................... A61F 5/0111 |
| | | 602/14 |
| 2005/0113729 A1 | 5/2005 | Scott et al. |
| 2007/0179521 A1 | 8/2007 | Horvat |
| 2010/0042026 A1 | 2/2010 | Kloecker et al. |
| 2011/0092872 A1 * | 4/2011 | Christiansen ....... A61F 13/0273 |
| | | 602/53 |
| 2013/0245517 A1 * | 9/2013 | Eddy .................... A47C 7/022 |
| | | 601/136 |

* cited by examiner

FIG. 1A
NORMAL
FIG. 1B
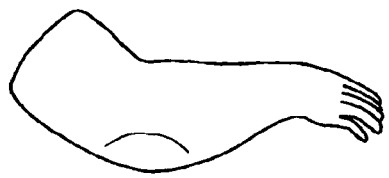
LYMPHEDEMA
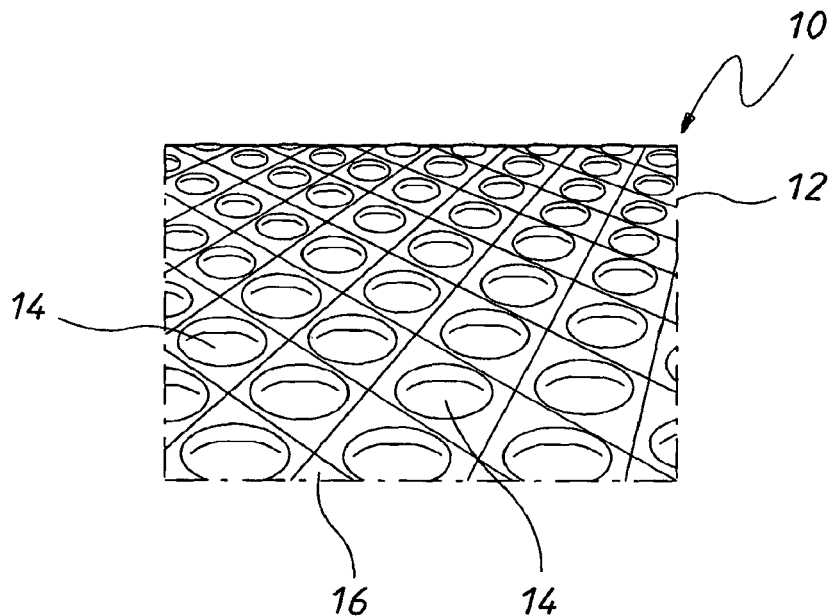
FIG. 2

THERAPEUTIC SUPPORT FOR BEING WORN BY A SUBJECT

CROSS REFERENCE TO RELATED APPLICATIONS

This application is a § 371 national stage entry of International Application No. PCT/AU2012/000931, filed Aug. 3, 2012, entitled "THERAPEUTIC SUPPORT FOR BEING WORN BY A SUBJECT," which claims priority to Australian Application No. AU 2012902897, filed Jul. 6, 2012, which are incorporated herein by reference in their entireties.

FIELD OF THE INVENTION

The present invention relates to a therapeutic support for use in situations where a subject has, or is at risk, of aberrant tissue fluid accumulation arising from surgery or other causes. A method for using the support in the prophylaxis or treatment of such fluid accumulation is also described.

BACKGROUND OF THE INVENTION

Oedema is the accumulation of fluid in tissues and/or cavities of the body producing swelling and can result from various causes such as injury, surgery, tissue inflammation, and systemic or local physiological conditions. Lymphoedema is one example of oedema.

The lymphatic system is part of the circulatory system and comprises a network of lymph vessels known as lymphangions which link lymph nodes together and function to return interstitial fluid to the bloodstream. Lymph nodes are organs of the immune system and are major sites of infection and toxin control by immune cells. Like veins, lymphangions have one-way valves to prevent backward flow. When blood passes through capillary beds under the action of the heart, blood plasma enters adjoining tissues delivering oxygen and nutrients. Most of this fluid is returns to veins but some (about 10%) remains. This fluid enters the lymphatic system taking with it proteins, fats, cellular substances and toxins that are transported to lymph nodes by lymph vessels, prior to the transport of the "lymph" fluid to the bloodstream. Bacteria and viruses can also be transported by the lymph vessels to lymph nodes where immune cells can respond. The lymphatic system does not have its own pump and lymph moves unidirectionally through lymph vessels by the contraction of muscles and body movements, and extrinsic compression of lymph vessels by externally applied forces.

Cancer cells can metastasise from the site of the primary tumor to remote areas in the body via the lymphatic system. As a result it is common practice such as in breast cancer to identify the "sentinal" lymph node(s) to which the lymph in the area of the cancerous tissue initially drain using weak radioactive and/or coloured dyes, and to remove those nodes. If cancer cells are found in the sentinal node(s) indicating invasive spread of the cancer and/or it is deemed warranted by the nature or extent of the cancer, upstream clusters of auxiliary lymph nodes can be removed in subsequent surgery. In the case of breast cancer, this is typically from the armpit region of the subject The removal of lymph nodes can substantially impair the ability of the lymphatic system to drain lymph from the affected area, resulting in stagnation and retention of lymph causing swelling (lymphoedema), and associated inflammation of tissues. More generally, lymphoedema is a condition that occurs when the lymphatic drainage system is impaired to the extent that the volume of lymphatic fluid within a given area exceeds the capacity of the lymphatic transport system to remove it. It has, for example, been reported that 25% of mastectomy patients develop lymphoedema, the development of which may take up to 3 years post surgery. Lymphoedema may also be caused by lack of muscle tone, certain diseases and conditions, tissue trauma arising from accidents, and for example, compromise of the lymphatic system due to cellulitis. There is no known cure for lymphoedema, and the symptoms can only be managed.

The swelling and inflammation associated with lymphodema can be painful and result in significant deformity of tissues and limbs causing substantial distress and incapacity to the sufferer. Tissues with lymphoedema are also at increased risk of infection. In more serious cases, fibrosis/hardening of the affected tissue can occur.

Lymphoedema is commonly treated with the intermittent use of compression bandaging, socks or sleeves, and/or gentle repetitive massaging of the area to drain the accumulated lymph. If the pressure applied is too great, lymphatic vessels can be overly compressed, blocking the lymphatic pathway. Conventional compression garments can be bulky thereby restricting movement of the subject, and may be uncomfortable or not suitable to wear in hot and/or humid climates. Sports compression garments typically provide little assistance to lymphoedema, and it is believed there are no compression garments that are generally commercially available that assist with the treatment of lymphoedema of the lower torso and genital area. Moreover, lymphatic massaging requires training to master, is time intensive, and only lasts as long as the massaging session.

Hence, whilst such current treatments are useful, they may only be of limited assistance and there is an ongoing need for improved or alternate therapies for lymphoedema.

SUMMARY OF THE INVENTION

In an aspect of the invention there is provided flexible support for the prophylaxis or treatment of the accumulation of a fluid in the body of a subject in need thereof, wherein the support has a plurality of protruberances for respectively applying localised pressure to an area of the subject's body with, or subject to, accumulation of the fluid, the support being configured to be worn by the subject over the area and press the protruberances against the body of the subject, and wherein the protruberances are spaced apart from one another about a face of the support.

In yet another aspect embodied by the invention there is provided a method for the prophylaxis or treatment of the accumulation of a fluid in the body of a subject, comprising:
 providing a flexible support having a plurality of protruberances for respectively applying localised pressure to an area of the subject's body with, or subject to, accumulation of the fluid, the protruberances being spaced apart from one another about a face of the support; and
 placing or fitting the support over the area whereby the support is retained in position and the protruberances press against said area, for the support to be worn by the subject. Typically, the protruberances are flexible and can be partially compressed when pressed against the body of the subject. Typically, the support comprises a backing about which the protruberances are spaced apart from one another. Most typically, the protruberances are arranged in a regular pattern about the backing.

Typically, the protruberances are defined by raised elements disposed on the backing.

Typically, the raised elements are fixedly mounted to the backing.

Typically, the support comprises front and rear layers of webbing between which the raised elements are retained, the rear layer of the webbing being the backing on which the raised elements are disposed, and the raised elements forming the protruberances in the front layer of the webbing.

Typically, the front and rear layers of the webbing are fixed together between the protruberances forming respective compartments of the webbing that house the raised elements.

Typically, the front and back layers of the webbing are secured together by seams. Most typically, the seams are sewn seams.

Typically, the front layer of the webbing generally conforms to the shape of the raised elements thereby forming the protruberances and restraining the raised elements against collapse.

The raised elements may be interconnected to one another. In at least some embodiments the raised elements can be fluid filled (e.g., gas filled). Respective of the raised elements can, for example, be a bubble defined by an outer membrane of the bubble.

Typically, the support is air and moisture permeable between respective of the protruberances in a direction from said face of the support to an opposite face of the support so as to be "breathable". Advantageously, this may reduce the risk of overheating and sweating under the support facilitating the wearing of the support in warm and/or humid climates.

In at least some embodiments, the support is adapted to receive, or be fastened about, the subject's body. Most typically, the support includes fastening means for retaining the support in position on the subject when the support is worn by the subject.

The support can, for example, be a garment (e.g., an outer garment or undergarment), a wrap, a sleeve, or a stocking.

The accumulated fluid may, for example, be aberant fluid accumulation causing oedema or other accumulated fluid such as lactic acid fluid build-up stemming from racing, running, exercise or sport, haemotomas and blood accumulation in varicose veins. Typically, the oedema is lymphoedema. However, the use of supports embodied by the invention is not limited thereto and in one or more forms may be used for oedema resulting from injuries to tissues or joints, surgery, tissue or joint inflammation, and other physiological conditions.

In yet another aspect there is provided webbing with a face having protruberances as described herein for use in the making of a therapeutic support embodied by the invention.

More broadly, in another aspect of the invention there is provided a flexible therapeutic support having a face with a plurality of raised protruberances for respectively applying localised pressure to an area of the subject's body, the support being configured to be worn by the subject over the area and press the protruberances against the body of the subject, and wherein the protruberances are spaced apart from one another about the face of the support.

In yet another aspect there is provided a method for therapeutic treatment of a subject, comprising providing a flexible support having a face with a plurality of raised protruberances for respectively applying localised pressure to an area of the subject's body for being treated by the support, the mounds being spaced apart from one another about the face of the support; and placing or fitting the support over the area whereby the support is retained in position and the protruberances press against said area, for the support to be worn by the subject.

Advantageously, in one or more forms, a support embodied by the invention differs from a conventional compression bandage, sleeve or the like by respective of the protruberances of the support each providing localised pressure to the region of the subject's body on which the support is worn. That is, the pressure applied is not constant across the support as is generally the case for conventional compression bandaging/sleeving, there being regions between the protruberances of less or no applied pressure. This reduces the risk of lymphatic vessels or other fluid drainage pathways being essentially "closed" by continuous over compression as may occur with the use of conventional compression bandaging or sleeving. In at least some embodiments, a support in accordance with the invention may assist treating oedema or other forms of fluid accumulation in subjects for whom the use of compression bandaging or sleeves provides no or only limited benefit, or by the nature or location of the oedema or accumulated fluid, the use of conventional compression bandaging or sleeving is not suitable or practical.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers, integers or steps.

Any discussion of documents, acts, materials, devices, articles or the like that has been included in this specification is solely for the purpose of providing a context for the invention. It is not to be taken as an admission that any or all of these matters form part of the prior art base or were common general knowledge in the field relevant to the invention as it existed in Australia or elsewhere before the priority date of this application.

The features and advantages of the invention will become further apparent from the following detailed description of embodiments thereof together with the accompanying drawings wherein different components and/or embodiments having the purpose or function may be numbered similarly.

BRIEF DESCRIPTION OF THE ACCOMPANYING DRAWINGS

FIGS. 1A and 1B illustrate an arm of a human subject with lymphedema (FIG. 1B) compared to a normal arm (FIG. 1A);

FIG. 2 is a partial view of the mounds of a fabric for use in providing a therapeutic support embodied by the invention for the prophylaxis or treatment of lymphoedema in a subject;

DETAILED DESCRIPTION OF EXEMPLARY EMBODIMENTS OF THE INVENTION

A fabric 10 that can be used in the manufacture of a therapeutic support embodied by the invention as described herein is shown in FIG. 2. The face 12 of the fabric has a plurality of protuberances in the form of mounds 14 that are spaced apart from one another about the face whereby they form a regular pattern of rows in both the cross-wise and length wise direction of the fabric, the mounds being interconnected to one another by the webbing 16 from which the fabric is made.

Figure 3:
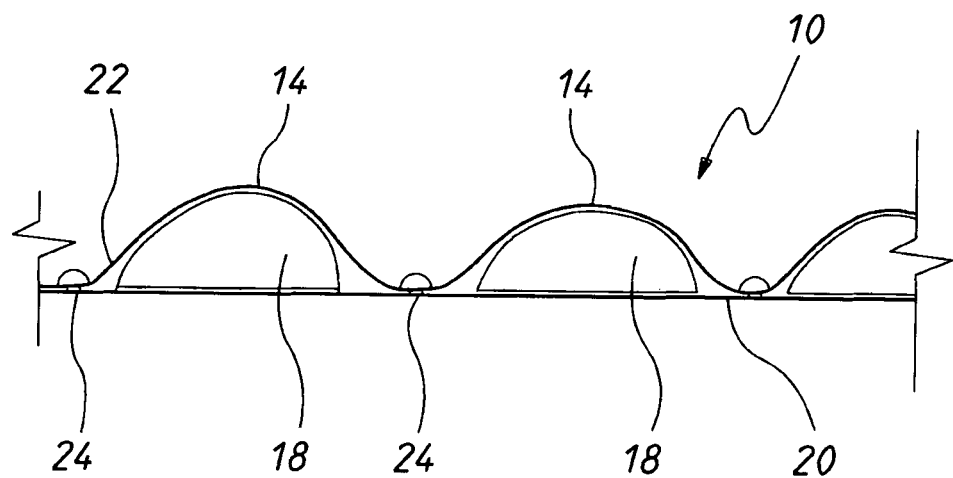
FIG. 3 is a diagrammatic cross-sectional side view side of protruberances in the form of mounds of the fabric of FIG. 2.

In the embodiment shown, each mound 14 is formed by a respective raised mound shaped element in the form of a gas-filled "bubble" or blister 18 retained in position between front and rear layers 22 and 20 of the webbing 16 as illustrated in FIG. 3. More particularly, each bubble 18 comprises a sealed enclosure defined by an outer plastic membrane and which is disposed on the rear layer 20 of the webbing. In order to retain the bubbles 18 in position, the front layer 20 of the webbing is sewn to the rear layer 22 defining seams generally indicated by the numeral 24 between respective of the rows of the mounds 14 whereby the front layer of the webbing generally conforms to the dome shaped profile of the bubbles forming individual closed compartment each housing a single bubble 18. The compartments thereby relatively closely envelope the respective bubbles. Although the bubbles/blisters may be partially compressed, the outer membrane of the bubble/blister is of a thickness and strength to restrain the bubble against complete collapse in use. Whilst each bubble 18 is generally dome shaped with sides that taper to a rounded apex, mound shaped elements with a flattened or concaved apex or which, for example, are generally frustonical in form, may also be utilised.

In the embodiment shown, the front and rear layers 22 and 20 of the webbing each consist of relatively lightweight cotton cloth. As such, the fabric 10 is soft to the touch and is permeable to air as well as moisture which may arise due to perspiration when the fabric is worn, and so is "breathable". Accordingly, the fabric and a therapeutic support in accordance with the invention that is made from it are suitable for being worn in warm and/or higher humidity climates such as occur in many parts of Australia and elsewhere during the summer months.

A jig can be used for manufacture of a therapeutic support as described herein wherein the jig as a plurality of spaced apart openings for individual placement of the mound shaped elements such that they protrude rearwardly from the jig. A heat reactive Adhesive (e.g., a quilting appliqué such as ODIF 606™ spray-on adhesive, Odd, New Milford, Conn., USA) is applied to their exposed rear surface, and a rear layer 20 of fabric webbing is laid flatly over the mound elements. Heat is then applied to that layer of webbing to activate or set the adhesive whereby the mound elements are fixed to the webbing. This can be readily achieved by ironing the rear layer of the webbing. The webbing is then removed from the jig and laid flatly with the attached mound elements facing up, an excess length of the webbing is folded over the mound elements to provide a front webbing layer 22, and the layers of the webbing are sewn together as described above. Whilst heat reactive adhesive is particularly suitable for fixing the bubbles 18 to the rear layer of the fabric, any suitable adhesive may be used. Moreover, and suitable method for fixing the front and rear layers 22, 20 of the webbing together can be employed. For example, seams fixing the front and rear layers of the webbing together may be formed by heat or sonic welding rather than by sewing the layers together.

Suitable "bubbles" 18 that can be utilised in the manufacture of the fabric 10 can be provided by plastic air cell sheeting conventionally used for covering swimming pools. The "bubbles" of plastic air cell sheeting used for packaging and for wrapping delicate or breakable items for storage or transport purposes may also be used provided the plastic membrane of the bubbles is of sufficient thickness and strength with withstand the pressures applied to the bubbles during use of a therapeutic support of the invention. However, as plastic is impermeable to air and moisture, the bubbles of the wrapping are generally cut intact from the sheeting and sewn either individually or in the form of perforated individual rows into position in the webbing 16 such that the wrap does not form a continuous impermeable plastic barrier across that area of the fabric presenting the bubbles 18. In still other embodiments, a sheet of bubbles or other mound shaped elements that are interconnected by fine (e.g., plastic) strips, tendrils or filaments, or which is otherwise perforated between the mound shaped elements to provide adequate ventilation/permeability through the sheet may be employed in a therapeutic support in accordance with the invention. Rather than "bubbles" 18, the raised mound shaped insert elements can be in the form of mounds formed of an open or closed-cell foamed plastics material of a predetermined density (either as individual mounds or in sheet form), or other suitable material (e.g., polyurethane or rubberised plastics).

In use, a therapeutic support embodied by the invention is worn by the subject such that the mounds are in direct contact with the subject's skin over the area to be treated so as to be pressed against the skin so as to form dimple like depressions in the skin. It is not necessary that the mounds be pressed against the skin with the same level of pressure as a compression bandage or stocking, only a firm pressure against the skin is desirable. In instances where, for example, oedema has arisen as a result of surgery, depressions or cavities may be formed in the subject's body as a result of tissue removal (e.g., a depression in the chest wall as a result of a mastectomy), such that the mounds of the support either do not press against that region or only contact that region with less than optimum pressure. To address this, a support embodied by the invention can be provided with padding arranged to press the affected mounds into the depression or cavity so as to make firm contact with the skin. For example, the support can be provided with a rear pocket into which the padding can be inserted. The padding can, for instance, be a prosthesis such as a breast prosthesis, a gel or fluid filled padding element, or fabric padding. Rather than being provided in a pocket of the support, the padding can be sewn or otherwise incorporated into the support.

The support can be worn over the region of the body exhibiting, or which is otherwise subject to, fluid accumulation and/or the region of the subject's body where a blockage or tissue damage (e.g., scar tissue) responsible for oedema or fluid accumulation whether with or without visible associated symptoms such as noticeable swelling is located (e.g., a site of surgery). For example, where a subject has lymphoedema in the arm due to removal of auxiliary lymph nodes in the armpit region, the wearing of a support in accordance with the invention pressed against the area of surgery in the armpit or chest side wall may be sufficient to assist drainage of accumulated fluid in the arm itself by acting on scar tissue to at least partially open lymph vessels and/or other fluid drainage pathways for passage of the accumulated fluid from the subject's arm, even though that area does not exhibit oedema itself. The therapeutic support in such instances may be an insert fitted inside a brassiere or other undergarment as described further below. However, the subject may also wear a sleeve embodied by the invention on their affected arm to alleviate the observed swelling in the arm, though this may not be necessary in all cases. In at least some embodiments, a therapeutic support as described herein can be provided for being worn over the oedema affected area and an adjacent region of the body which has a blocked or restricted fluid drainage pathway responsible for that oedema.

Further examples of areas of a subject's body which may be responsible for oedema but which may or may not exhibit swelling or other symptoms of oedema are the torso and groin areas. In these instances, a fluid pathway blockage in these areas such as may arise from surgery can result in oedema in one or both legs of the subject (e.g., the upper thigh, lower thigh and/or lower leg region(s)). In these situations, the subject may wear a support embodied by the invention to treat the observed swelling resulting from the oedema and/or the site of the fluid drainage pathway blockage or obstruction(s) in the groin or torso area.

Figure 4:
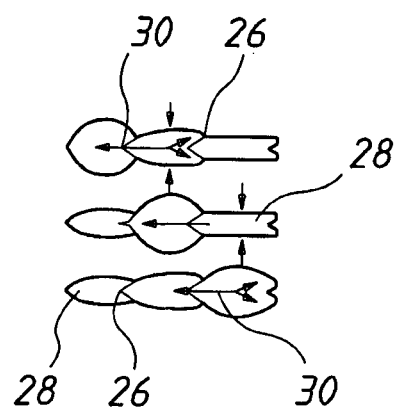
FIG. 4 is a diagrammatic view illustrating a lymphatic vessel.

A diagrammatic view of a lymphatic vessel is illustrated in FIG. 4. The vessel comprises one-way valves indicated by the numeral 26 which can generally be viewed as defining respective compartments 28 along the vessel. In normal lymphatic vessels, lymph moves through each valve from one compartment to the next as indicated by the arrows 30 by the effect of muscle contractions and body movement as outlined above. In lymphoedema, however, the flow of the lymph is impeded, such as by scarring, blockages, and the removal of lymphatic vessel pathways arising from surgery.

Figure 5:
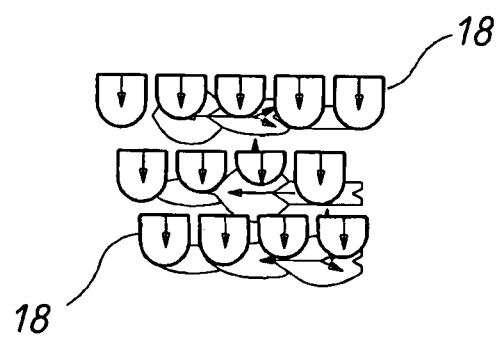
FIG. 5 is a diagrammatic view illustrating the hypothesised mode of action of the protruberances of a therapeutic support embodied by the invention in the prophylaxis or treatment of lymphoedema.

Without being limited by theory, it is believed the mounds of a support embodied by the invention act to apply gentle but firm localised pressure to tissues and lymphatic vessels whereby in the case of lymphoedma, lymph is progressively driven along the vessels and drained from the affected tissue or limb as generally illustrated by FIG. 5. This allow more interstitial fluid to enter the lymphatic vessels from the surrounding tissues which in turn is progressively driven along the vessels by the mounds 14 of the support, incrementally reducing the accumulated fluid in the tissue or limb and the associated swelling. More particularly, as indicated by FIG. 5, it is thought by the inventor that muscle movement of the subject whilst undertaking their normal daily activities when wearing the support results in repetitive differential pressures being applied to the subject by respective of the mounds and/or concomitant slight movement in the location of the pressure applied by ones of the mounds at different times. In any event, it is believed the localised pressure applied to the subject by each mound causes the lymph to be progressively driven along the underlying lymphatic vessels from one compartment to the next, the return flow of the lymph being inhibited by respective of the one-way valves of the lymphatic vessels. Moreover, the respective areas of localised pressure applied by the mounds and slight movements of the mounds relative to the skin in use can be thought of as providing an effect akin to passive "massaging" of the tissue or limb affected by the oedema, the massaging continuing for as long as the support is worn. Hence, whilst embodiments of therapeutic support as described herein have particular application to the prophylaxis or treatment of lymphopedema, they may also be used for other forms of oedema such as accumulated tissue fluid due to swelling arising from sprains and other tissue injuries, as well as to alleviate the build-up of lactic acid that may occur following racing, sports, or exercise and, for instance, the passive massaging of varicose veins or other vascular conditions to assist passage of blood through such vasculature.

Accordingly, the invention also extends to the provision and use of therapeutic supports herein for effecting passive massaging of body tissues. More specifically, in another aspect of the invention there is provided a flexible support for effective passive massage of the body of a subject, wherein the support has a face with a plurality of raised protruberances for respectively applying localised pressure to an area of the subject's body, the support being configured to be worn by the subject over the area and press the protruberances against the body of the subject, and wherein the protruberances are spaced apart from one another about the face of the support.

Still further, there is provided a method for effecting passive massage of the body of a subject, comprising providing a flexible support having a face with a plurality of raised protruberances for respectively applying localised pressure to an area of the subject's body, the mounds being spaced apart from one another about the face of the support; and placing or fitting the support over the area whereby the support is retained in position and the protruberances press against said area, for the support to be worn by the subject.

Figure 6:
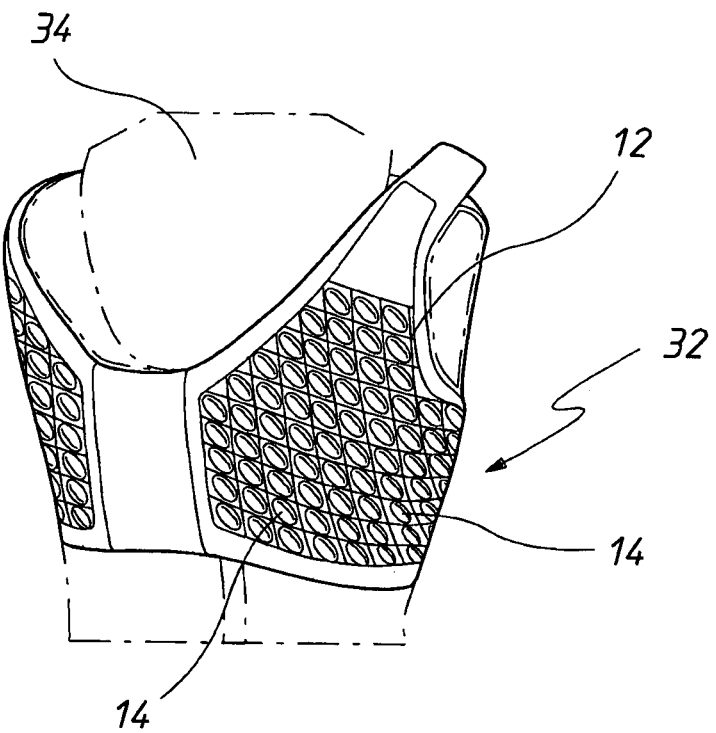
FIG. 6 shows a front view of a garment embodied by the invention in the form of a brassier type therapeutic support fitted inside out to the torso of a mannequin for demonstration purposes.
Figure 7:
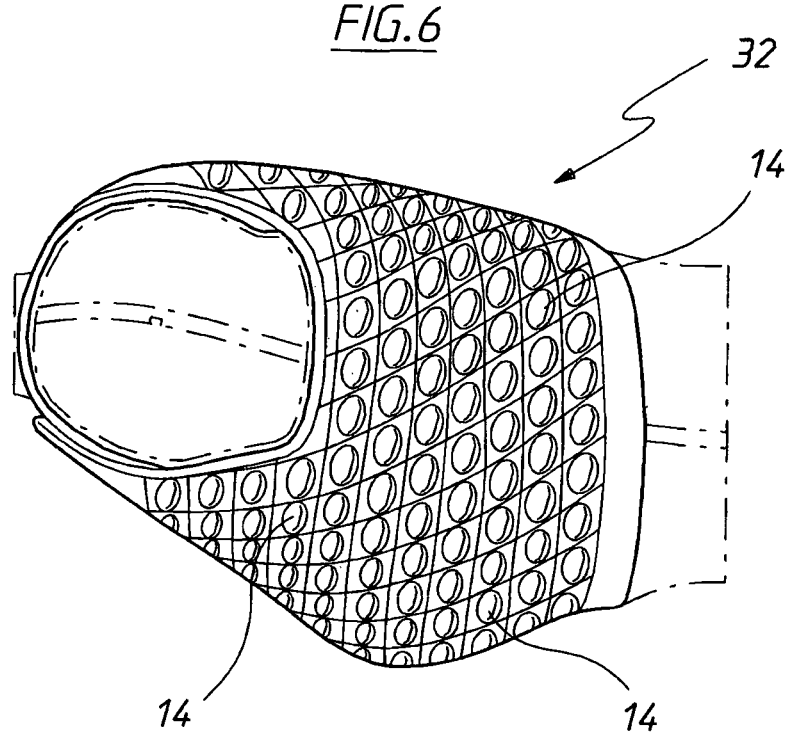
FIG. 7 is a side view of the garment of FIG. 6 fitted to the torso of the mannequin.

An example of a therapeutic support 32 embodied by the invention is illustrated in FIG. 6 and FIG. 7. In this instance the support 32 is a brassier type garment suitable for use in the prophylaxis or treatment of lymphoedema or other forms of oedema in the chest wall and/or under arm region of the upper torso, as may occur following a mastectomy and removal of auxiliary lymph nodes for the treatment of breast cancer. The brassier support 32 is configured to be fitted to the subject such that the front face 12 of the fabric 10 presenting the mounds 14 is pressed against the relevant area of the subject's body. Fastening means in the form of a hook and loop tape fastening system (e.g., Velcro™) is provided on the shoulder region of the garment to allow the subject wearer to fasten the support in position in a firm but comfortable fit. The garment support 32 is shown fitted to the mannequin 34 in reverse in FIG. 6 and FIG. 7 so that mounds 14 of the garment may be readily visualised.

It will be understood that a therapeutic support 32 embodied by the invention may be provided in various different forms. For example, the support may be a garment such as a brassier type undergarment as shown in FIG. 6, a singlet type top, a corset, vest, a shoulder type support, underpants (e.g., briefs or shorts) for prophylaxis or treatment of lymphoedema or other form of oedema in the genital area, T-shirts, stocking(s) for one or both legs, pants, a sleeve such as for the arm of a subject (e.g., both the lower and upper arm), a sock, and so on. In other forms; the support may be in the form of a wrap comprising a length of fabric 10 for being wrapped around the relevant body area (e.g., the lower abdomen or chest region) and fastened in position by suitable fastening means such as a hook and loop tape fastening system as described above or other fastening system such as press studs and the like. It is not necessary that the support wrap around the entire relevant body portion of the subject.

Figure 8:
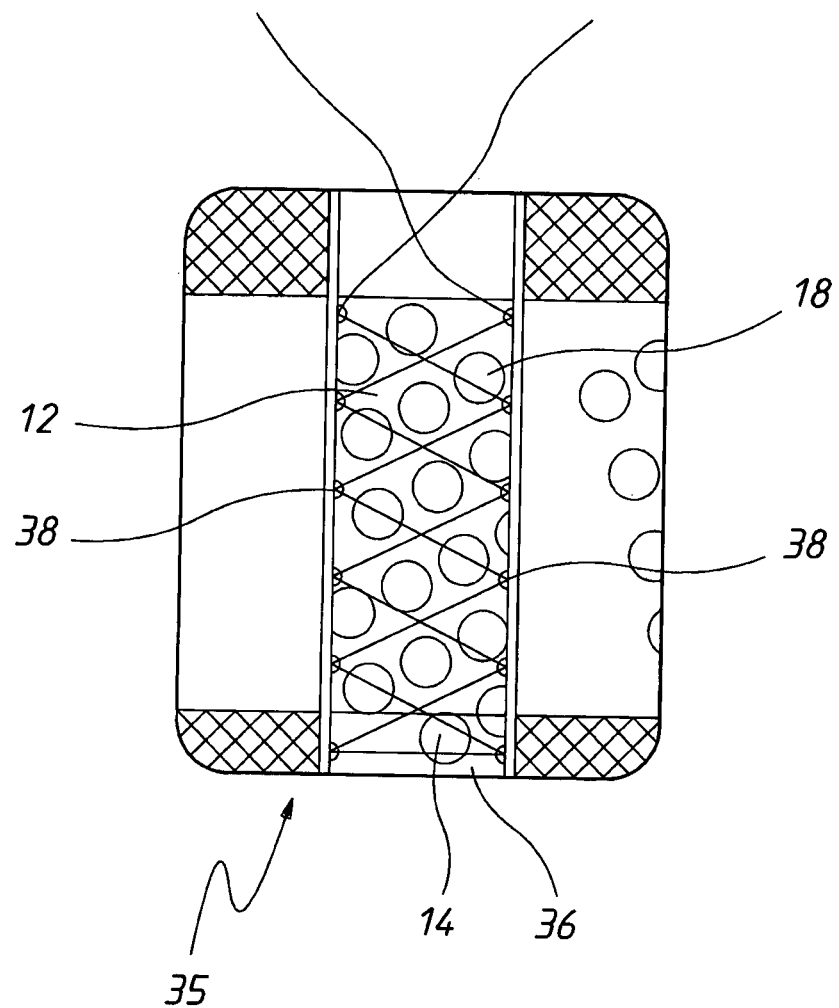
FIG. 8 is a diagrammatic side view of another garment embodied by the invention.
Figure 9:
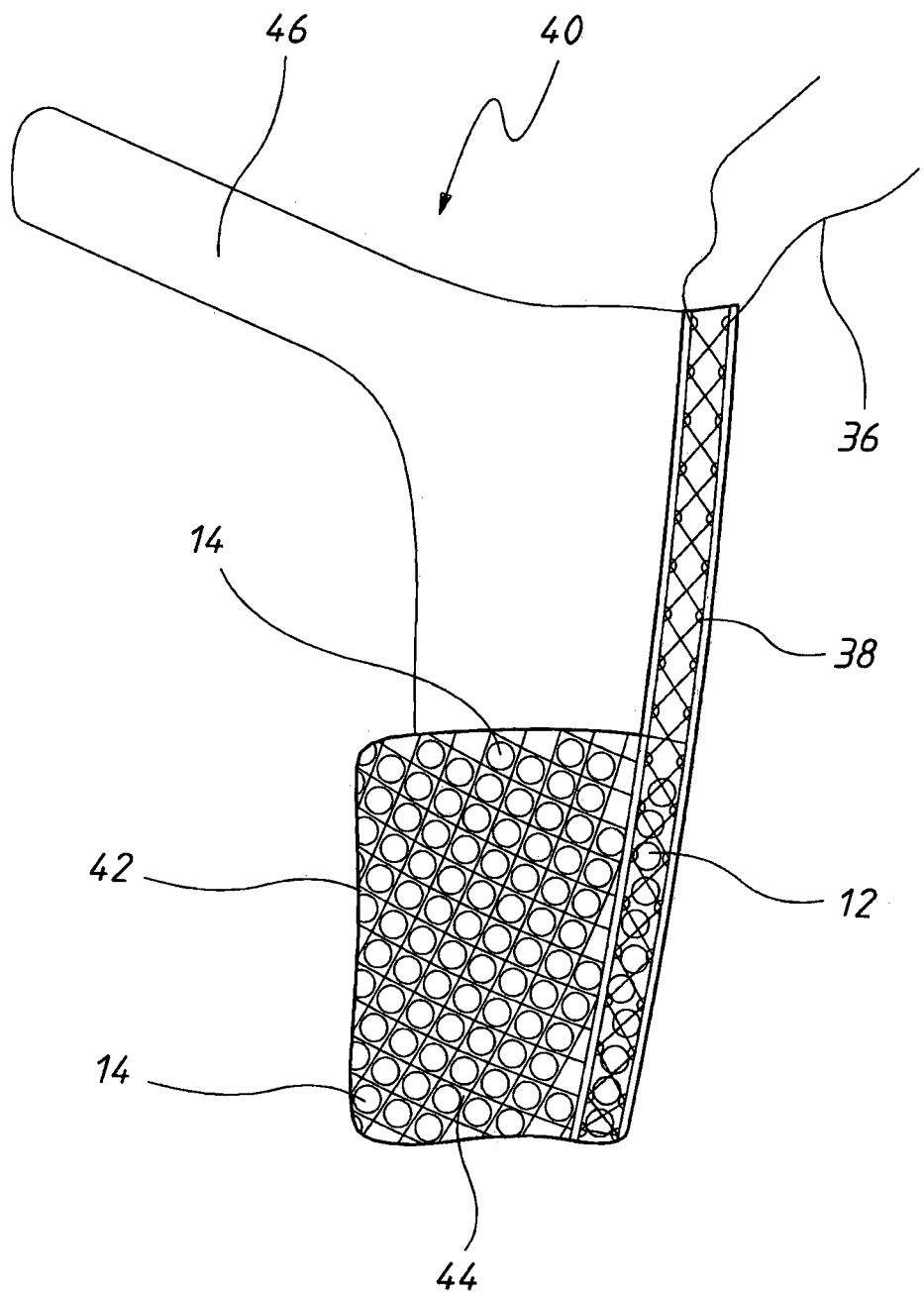
FIG. 9 is a diagrammatic view of another garment embodied by the invention.

A further therapeutic support embodied by the invention in the form of a wrap 35 for being worn over the upper thigh region and having a ribbon 36 threaded through spaced apart islets 38 for being tightened and tied to hold the support in position whilst being worn is shown in FIG. 8. Yet another embodiment is shown in FIG. 9. In this instance, the support 40 is in the form of an undergarment comprising a leg section generally indicated by the numeral 42 with a panel 44 having mounds 14 for being wrapped around the lower thigh area above the knee of a subject. A strap 46 is provided for being fastened around the waist of the subject and as with the support shown in FIG. 8, a ribbon 36 is provided for tightening the support when worn. In a variation of this embodiment, the panel 44 can be longer so as to extend from below the knee to the upper thigh region of the subject. In addition, for example, underpants can be provided with a panel having mounds 14 for being pressed against the groin region of the subject wearing them for the prophylaxis or treatment of oedema (e.g., lymphoedema) in that area.

Figure 10:
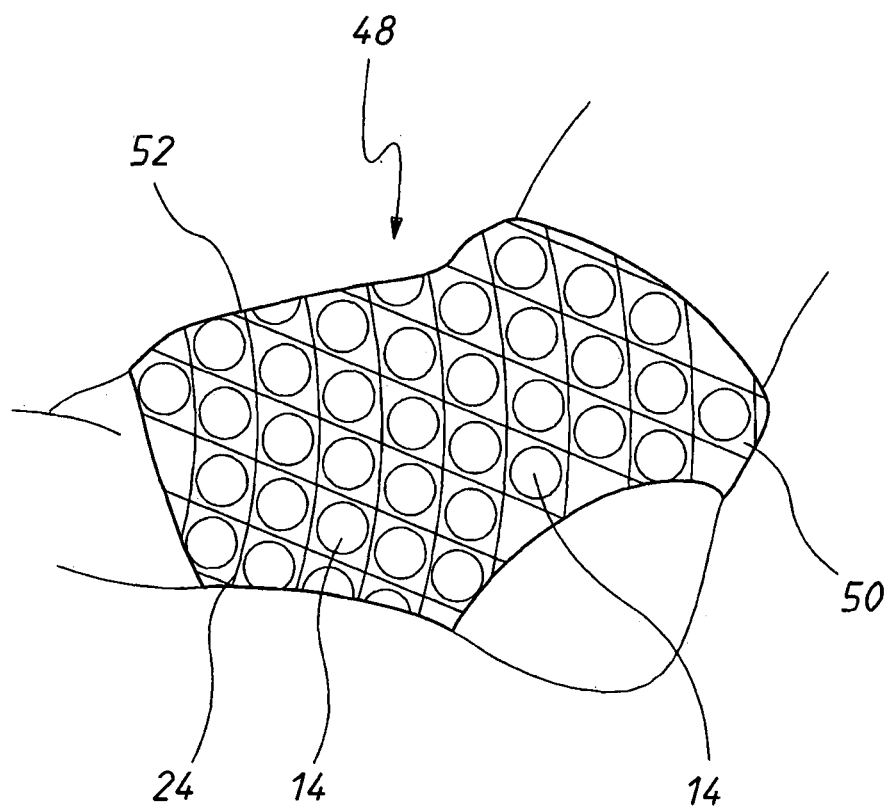
FIG. 10 is a diagrammatic view of another support embodied by the invention for treating oedema in the arch and ankle of a foot.

Still another embodiment is shown in FIG. 10. In this instance, the support 48 is for treating oedema in the arch and ankle region of a foot. To fasten the support in position, a strap 50 is wrapped around the ankle and a flap of the support indicated by the numeral 52 is wrapped over the arch of the foot, the strap and flap being fastened in position by respective hook and loop fastening systems. For treatment of oedema in the ball region of the sole, a support embodied by the invention of the type shown in FIG. 10 can be provided whereby mounds 14 are positioned so as to press against the ball region.

Figure 11:
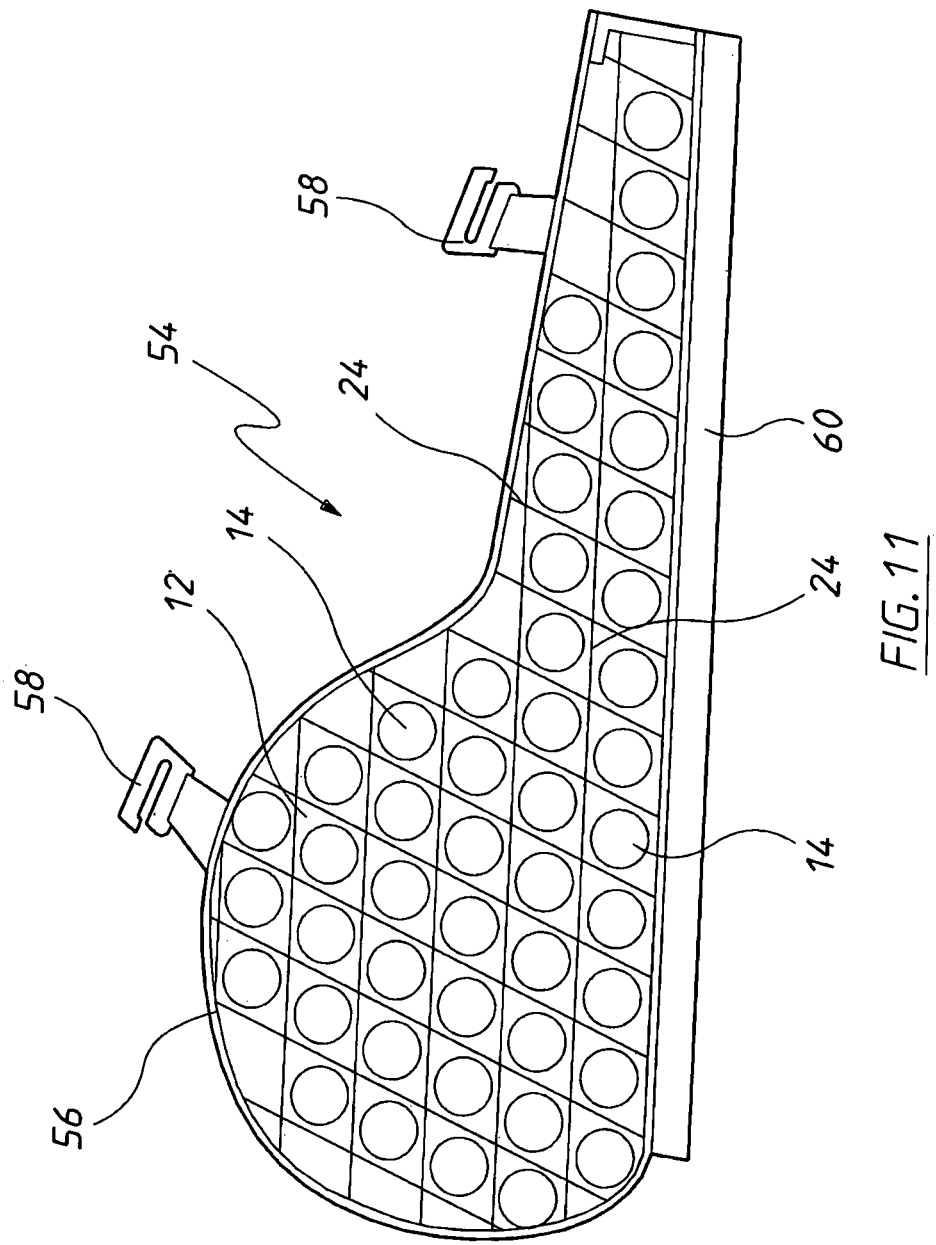
FIG. 11 is a diagrammatic front view on a support embodied by the invention in the form of an insert to be worn in a brassier for treatment of lymphoedema in the right breast and underarm region of a subject.

In addition, the invention extends to the provision and use of supports for being inserted into, or otherwise fitted to, undergarments or other garments as described herein. An example of this type of therapeutic support is shown in FIG. 11 for being fitted to a brassier. More particularly, the support insert 54 includes a breast section 56 with a rear pocket (not shown) for insertion of a breast prosthesis, and an elongate section extending therefrom for being wrapped around the underarm region of the subject under the strap of the brassier whereby the brassier strap presses mounds 14 against the skin of the subject: Clips 58 are provided for clipping the insert 54 to the brassier whereby the breast section 56 is positioned across the relevant breast cup of the brassier. To further secure the insert 54 in position, the lower margin 60 of the insert can be wrapped about the lower edge of the brassier and also fastened to the brassier by suitable clips or other fastening system (e.g., press studs, Velcro™ etc). In at least some embodiments, inserts in accordance with the invention can be clipped or fastened to convention garments, undergarments (e.g., brassiers, underpants etc), wraps and the like, and be worn by a subject as described herein.

As yet another embodiment, an insert with integrally formed mounds 14 can be inserted are fastened to a garment, wrap or the like to form a therapeutic support in accordance with the invention.

Typically, a support or support insert in accordance with the invention does not include any band (e.g., of elastic or the like) that when the support/insert is worn wraps around the subject forming a band of constriction in the subject's skin, as this may impede or potentially block the passage of accumulated oedema fluid under the band and thereby, the action of the support or insert.

Whilst cotton cloth is particularly suitable for use as the webbing 16, other materials can be employed such as cloth made from other natural and/or synthetic fibres and yarns (e.g., nylon, polyester, rayon, acrylic fibre, viscose and spandex), woven or felted materials, elastomeric materials, and combinations of such fibres and materials (e.g., bamboo cotton spandex combinations). Hence, the term "webbing" as used herein is to be taken to encompass any material deemed suitable for use in a support embodied by the invention, and is not to be restricted to a particular cloth, material or the like unless otherwise expressly stated or implied herein. When the fabric 10 is fabricated from synthetic fibres it may include a layer of cotton or other suitably soft material for contact with the skin of the subject for reasons of comfort.

The care of subjects/patients post operatively typically involves education about the risk of developing oedema, identification of the symptoms of oedema, and physiotherapy for e.g., scar tightness, cording (i.e., a sensation of a "cord" across the chest restricting arm movement), seroma development, and/or muscle tightness. The development of oedema post surgery (e.g., following removal of auxiliary lymph nodes) can take a number of years. However, there can be a sudden onset of the swelling associated with oedema, and a subject may not be aware that the oedema has been developing until noticeable swelling occurs. For example, there can be accumulation of fluid in the torso area but the presence of oedema may only become apparent with swelling of the leg or legs of the subject.

It is thought that regular gentle lymph drainage massaging of the wound and tissues proximal thereto during and post healing of the wound may assist in maintaining open, or otherwise developing, lymph and/or other drainage pathways through the wound area thereby in at least the case of lymphoedema, lessening the risk of lymphoedema occurring or potentially avoiding the development of lymphoedema in the subject altogether. The wearing of a support embodied by the invention may facilitate this. In any event, the wearing of a support embodied by the invention for prophylaxis of lymphoedema is to be taken in its broadest sense as encompassing use of the support to maintain existing oedema at a reduced, controlled level, and for instance, to ameliorate existing oedema.

Whilst a therapeutic support embodied by the invention is particularly suitable for the prophylaxis or treatment of oedema (e.g., lymphoedema and other forms of oedema) in humans (both male and female), the invention is not limited thereto and extends to the provision and use of therapeutic supports as described herein on non-human mammals such as, but not limited to, horses, greyhounds and companion animals (e.g., dogs and cats) and, for example, members of the bovine, porcine and primate animal families. Indeed, at least some embodiments of therapeutic supports embodied by the invention may have application in alleviating build-up of fluid with high levels of lactic acid in tissues in athletes or animals (e.g., greyhounds and race horses) following training, exercise or racing. Likewise, embodiments of the invention may find application in treating other conditions in which passive massage by the supports may be of assistance such as in the treatment of varicose veins (e.g., blood pooling in varicose veins and associated varicose vein pain).

Whilst the protruberances of the embodiments described above are mound shaped, therapeutic supports embodied by the invention may be provided with protruberances that are other than mound shaped. Indeed, protruberances of any suitable shape that may be utilised (e.g., e.g., protruberances having a pyrimidal shape or a triangular, oval, elliptical, or generally square transverse cross-section).

From the above description it will be apparent that embodiments of therapeutic supports in accordance with the invention may provide one or more of the following advantages:
- An alternative to conventional compression bandaging for the prophylaxis or treatment of oedema, and particularly lymphoedema;
- An option for the treatment of oedema resistant to compression bandaging or compression sleeve treatment, or for which conventional compression bandaging or sleeve treatment is not suitable or provides little benefit;
- The treatment of the oedema is essentially continuous whilst the therapeutic support is worn by the subject;
- The therapeutic support may provide "passive" fluid (e.g., lymph) drainage massaging whilst being worn;
- There is no special training required;
- The provision of the mounds 14 may avoid or lessen the risk of lymphatic vessel(s) and/or fluid drainage pathway(s) being held continuously closed for the duration the support is worn as a result of compression applied by the support, as may occur with the use of conventional compression bandaging or compression sleeving.
- The fabric 10 used in the support is "breathable", lessening the risk of sweating or overheating under the support occurring;
- The support can be lightweight and unobtrusive;
- A cost effective and readily accessible way of treating forms of oedema; and
- The support can be used in conjunction with other therapeutic treatments such as, but not limited to, massaging of the affected areas.

The invention will now be described further below with reference to a number of non-limiting Examples of the use of supports embodied by the invention.

EXAMPLES

Treatment of Lymphoedema in Human Subjects

Case 1

CP is a gynaecological cancer patient and was suffering with lymphoedema in her groin and abdomen. Her initial management of lymphoedema involved the use of conventional compression garments which was unsuccessful. Underpant supports with "bubble panels" in accordance with the present invention were worn by CP for two years and found to control the lymphoedema. CP found that lymphatic fluid built up in her abdomen rendering her much discomfort during periods in which the garment was not worn.

Case 2

GS is also a gynaecological cancer patient. She had tried several ways (including compression garments) to reduce her leg and abdominal lymphoedma. After wearing an underwear support garment having panels with mounds for being pressed against affected areas in accordance with the invention she has reduced lymphoedema, and is now on the lowest level of compression stockings, and is expected to not require the stockings in the near future. Her leg and abdominal swelling has reduced as well as physical discomfort that she previously experienced. GS also noted that when she stopped wearing the support, her swelling accumulated back to the original level which was painful and uncomfortable for her.

Case 3

SF had a swollen foot and ankle arising from reconstructive surgery. After wearing an ankle and foot support in accordance with the invention the fluid retention problem rapidly disappeared.

Case 4

BS suffered from lymphoedema in her leg and tried wearing an underwear garment in accordance with the invention but as she did not receive instant relief she instead chose to wear compression stockings recommended by her physiotherapist. BS was also undergoing weekly dialysis treatments and so was not a suitable candidate for trial with the underwear garment.

Case 5

K is a young girl and suffered from lymphoedema around her knee, ankle and foot after sustaining an injury 3 years previously. Pursuant to wearing an ankle and foot support and then a knee wrap in accordance with the invention, K had a reduction in swelling of her foot and ankle of approximately 2.5 cm, improved movement in her knee, ankle and foot, and no pain or tightness in her leg after 2 weeks of wearing the support(s).

Case 6

KB suffered from breast cancer and had a left mastectomy with auxiliary node clearance in 2001 followed by chemotherapy treatment over a period of 4 months. As a result of her surgery, she developed lymphoedema in her left underarm region. She managed her lymphoedema with regular fortnightly remedial massage which gave given her limited relief for a short amount of time. KB also trialled a compression bandage (from a physiotherapist) but felt that the bandage only aggravated the problem.

KB started wearing a brassier style support with appropriately located panelling according to the invention in October 2010 and felt that she had improvement within the first few days of wearing the support. She also found that she had longer periods where she was not conscience of any sensation of lymphatic fluid build-up. KB noted that whilst the support did not stop this sensation completely, it was a welcome improvement that resulted in her experiencing longer periods of time when she completely is unaware of any fluid build-up. After 9 years of persisting with alternative management, she considered her quality of life has been enhanced considerably by wearing the support embodied by the invention which gave her quality relief that she previously did not have.

Case 7

SP is a breast cancer patient who developed lymphoedema in her left arm post surgery, the lymphoedema being of a level that she was unable to work in her profession as a Midwife. Since wearing a brassiere insert embodied by the invention, SP has ceased wearing conventional compression bandaging altogether and has returned to midwifery. SP indicated that whilst fluid accumulates when she "goes to the gym" or doesn't wear the support, the fluid soon dissipates once she wears the support enhancing her quality of life.

As will be understood, various changes and modifications may be made to embodiments of the invention described above without departing from the scope of the invention. Accordingly, the above embodiments are to be taken in all respects as merely illustrative and not restrictive.

The invention claimed is:
1. A garment adapted for the prophylaxis or treatment of the accumulation of fluid in an area of a subject body, the garment comprising a flexible support and means for fitting the flexible support to the body area, the support being formed from an outermost front layer of webbing and an outermost rear layer of webbing, said support having a plurality of spaced apart foam protuberances formed by raised elements disposed on the rear layer of the webbing and each having an upper outermost surface extending toward the front layer of the webbing, the front and rear layers of webbing being directly adhered together in areas between the raised elements, so that the front layer of the webbing conforms to the shape of each of the raised elements over its upper outermost surface, so as to present said protuberances on an inner surface of the support to face the body area, wherein the areas adhered between the raised elements having perforations to provide ventilation through the front and rear layers of webbing, the protuberances being flexible and adapted to be partially compressed when fitted against the body area so as to operatively apply localized pressure to the body area, whereby movement of the subject body induces a passive massaging action by the protuberances.

2. A garment according to claim 1, wherein the raised elements are fixedly mounted to the rear layer of the webbing on respective lower outermost surfaces of the raised elements, and the front layer of the webbing conforms to the shape of the raised elements over the entire upper outermost surface of each of the raised elements.

3. A garment according to claim 1, wherein the raised elements are mound shaped elements.

4. A garment according to claim 1, being air and moisture permeable between respective protuberances in a direction from said inner surface of the support toward an opposite outer surface of the support.

5. A garment according to claim 1, wherein the support is an undergarment.

6. A garment according to claim 1, wherein the protuberances are generally dome shaped.

7. A garment according to claim 1, wherein the body area has a deficient lymphatic system.

8. A garment according to claim 1, wherein the raised elements are constructed from a sheet of foam material on which the areas adhered between the raised elements are formed, leaving the foam material as the raised elements between the areas adhered between the raised elements.

9. A method for the prophylaxis or treatment of the accumulation of fluid in the area of a body of a subject in need thereof, comprising: supplying a garment, the garment including a flexible support, the support being formed from an outermost front layer of webbing and an outermost rear layer of webbing, said support having a plurality of spaced apart foam protuberances formed by raised elements disposed on the rear layer of the webbing and each having an upper outermost surface extending toward the front layer of the webbing, the front and rear layers of webbing being directly adhered together in areas between the protuberances, the front layer of the webbing conforms to the shape of each of the raised elements over its upper outermost surface, so as to present said protuberances on an inner surface of the support to face the body area, wherein the areas adhered between the raised elements having perforations to provide ventilation through the front and rear layers of webbing, the protuberances being flexible and adapted to be partially compressed when pressed against the body area so as to operatively apply localized pressure to the body area; fitting said garment to the body of the subject so as to operatively press the protuberances against the body area such that movement of the body of the subject induces a passive massaging action by the protuberances.

10. A method according to claim 9, wherein the raised elements are fixedly mounted to the rear layer of the webbing on respective lower outermost surfaces of the raised elements, and the front layer of the webbing conforms to the shape of the raised elements over the entire upper outermost surface of each of the raised elements.

11. A method according to claim 9, wherein the raised elements are mound shaped elements.

12. A method according to claim 9, wherein the support is air and moisture permeable between respective protuberances in a direction from said inner surface face of the support to an opposite outer surface of the support.

13. A method according to claim 9, wherein the support is an undergarment.

14. A method according to claim 9, wherein the body area has a deficient lymphatic system.

15. A method according to claim 9, wherein the raised elements are constructed from a sheet of foam material on which the areas adhered between the raised elements are formed, leaving the foam material as the raised elements between the areas adhered between the raised elements.

16. A garment adapted for the prophylaxis or treatment of the accumulation of fluid in an area of a subject body, the garment comprising a flexible support and means for fitting the flexible support to the body area, the support being formed from an outermost front layer of webbing and an outermost rear layer of webbing, said support having a plurality of spaced apart foam protuberances formed by raised elements disposed on the rear layer of webbing and each having an upper outermost surface extending toward the front layer of webbing, said support comprising an exterior surface configured to face away from the body formed from an outer surface of the rear layer of webbing, the front and rear layers of webbing being directly adhered together in areas between the raised elements, the front layer of webbing conforms to the shape of each of the raised elements over its upper outermost surface so as to present said protuberances on an inner surface of the support configured to face the body area, wherein the areas adhered between the raised elements having perforations to provide ventilation through the front and rear layers of webbing, and outermost surfaces of the areas adhered between the raised elements being formed by the outer surface of the rear layer of webbing and the inner surface of the front layer of webbing, the protuberances being flexible and adapted to be partially compressed when fitted against the body area so as to operatively apply localized pressure to the body area, whereby movement of the subject body induces a passive massaging action by the protuberances.

17. A garment according to claim 16, wherein the raised elements are constructed from a sheet of foam material on which the areas adhered between the raised elements are formed, leaving the foam material as the raised elements between the areas adhered between the raised elements.

18. A garment according to claim 16, wherein the raised elements are fixedly mounted to the rear layer of the webbing on respective lower outermost surfaces of the raised elements, and the front layer of the webbing conforms to the shape of the raised elements over the entire upper outermost surface of each of the raised elements.

* * * * *